(12) United States Patent
Malley

(10) Patent No.: US 6,397,492 B1
(45) Date of Patent: Jun. 4, 2002

(54) APPARATUS AND METHOD FOR PROCESSING MUNICIPAL SOLID WASTE

(75) Inventor: Donald E. Malley, Poplarville, MS (US)

(73) Assignee: MSW Patents, Inc., Montrose, AL (US)

(*) Notice: Subject to any disclaimer, the term of this patent is extended or adjusted under 35 U.S.C. 154(b) by 0 days.

(21) Appl. No.: 09/578,222

(22) Filed: May 23, 2000

Related U.S. Application Data

(60) Provisional application No. 60/136,287, filed on May 27, 1999.

(51) Int. Cl.[7] .................................................. B02C 1/00
(52) U.S. Cl. ............................ 34/411; 241/15; 241/18; 241/21; 241/65; 241/278.2; 241/220; 165/89; 165/90; 366/227; 366/59; 366/228
(58) Field of Search ............................ 34/380, 411–424, 34/476, 181, 241, 182, 183, 435, 434, 457, 87, 90, 122, 127, 129, 138; 241/15, 17, 18, 21, 23, 30, 47, 57, 65, 278.2, 220, 277

(56) References Cited

U.S. PATENT DOCUMENTS

| | | |
|---|---|---|
| 11,801 A | 10/1854 | Woolsey |
| 228,542 A | 6/1880 | Lister |
| 986,180 A | 3/1911 | Koenig |
| 1,381,802 A | 6/1921 | Copelin |
| 1,536,894 A | 5/1925 | Lillie |
| 4,342,830 A | 8/1982 | Holloway |
| 4,540,495 A | 9/1985 | Holloway |
| 4,844,351 A | 7/1989 | Holloway |
| 4,974,781 A | 12/1990 | Placzek |
| 5,116,363 A | 5/1992 | Romweber et al. |
| 5,119,994 A | 6/1992 | Placzek |
| 5,190,226 A | 3/1993 | Holloway |
| 5,253,764 A | 10/1993 | Gement |
| 5,300,438 A | 4/1994 | Augspurger et al. |
| 5,361,994 A | 11/1994 | Holloway |
| 5,407,809 A * | 4/1995 | Finn ........................... 366/228 |
| 5,427,650 A | 6/1995 | Holloway |
| 5,540,391 A * | 7/1996 | Anderson ..................... 241/21 |
| 5,556,445 A | 9/1996 | Quinn et al. |

* cited by examiner

*Primary Examiner*—Gregory Wilson
(74) *Attorney, Agent, or Firm*—Bradley Arant Rose & White LLP

(57) ABSTRACT

The present invention relates to an apparatus and method for separating and processing solid waste, often but not necessarily from municipalities (and so will be generically referred to herein as municipal solid waste or "MSW"), into useful products, and for reducing biohazards and putrid odors derived from MSW. The MSW is loaded into an elongated, generally cylindrically shaped rotating pressure vessel and is subjected to heat and pressure by the application of steam in specified amounts to break down the organic portion of the MSW into a cellulose feedstock, or a de-manufactured paper product, of uniform particle size and density. This product is then easily separable from other constituents of MSW, such as glass, aluminum and other metals, and plastics. The recyclables are recovered and sold in the market. The waste water from the process is reduced by processing through a water vamping apparatus. The apparatus and process disclosed herein, unlike any in the prior art, allows for an economically and technically viable industrial process and environmental solution, which have the potential to replace current landfill technology.

22 Claims, 2 Drawing Sheets

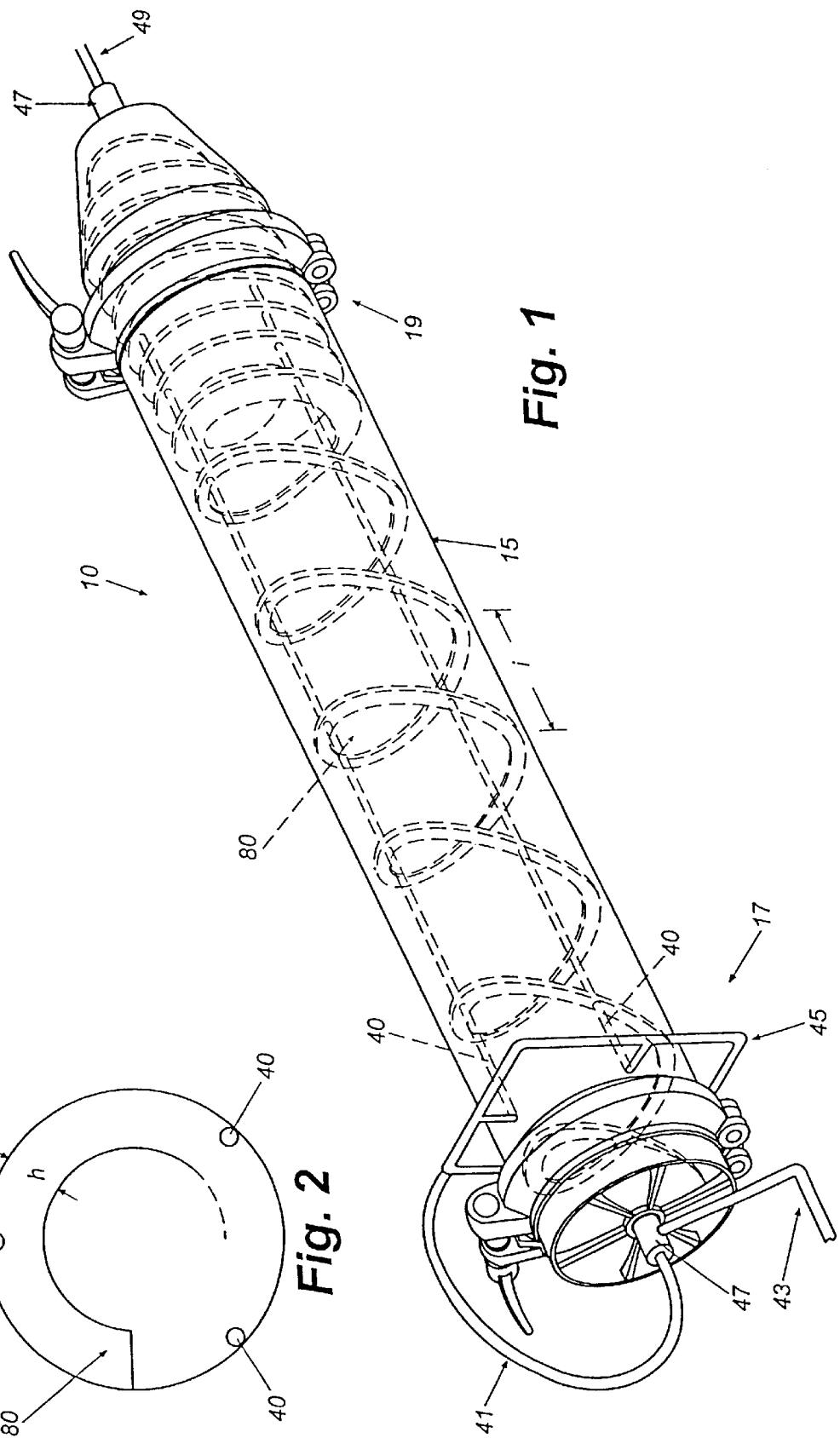

APPARATUS AND METHOD FOR PROCESSING MUNICIPAL SOLID WASTE

This application claims the benefit of the provisional application accorded Ser. No. 60/136,287 and filed on May 27, 1999 in the United States Patent and Trademark Office.

BACKGROUND

One of the major problems confronting society today is the generation of waste. Municipalities, by their very existence, generate waste that must be disposed of and the problem is compounding continually. According to some studies, the average person generates four (4) pounds of municipal waste per day. Historically, rivers have been fouled with waste, swamps have been filled, and air polluted by waste being burned in open pits. Governmental agencies have become increasingly aware of the cumulative effects of these activities in recent years and have begun to mandate controls for the disposal of waste.

Landfilling is the primary method of waste disposal, which sometimes unfortunately reflects a mentality of "out of sight—out of mind." When poorly contained landfills decompose, hazardous materials may find their way into the environment. Although technology is available to build safer landfills, there are fewer landfills today than here were ten years ago. It appears that landfills throughout the world are filling up.

The most commonly considered alternative to the landfill method is mass incineration and its related activity, the production of refuse derived fuel (RDF). Incineration and refuse derived fuel produce a variety of pollutants, which if improperly regulated or in high concentrations may cause respiratory discomfort and disease. These pollutants are believed to be caused by incomplete combustion of municipal solid waste and the combustion of plastics.

Solid waste products, often but not necessarily from municipalities (and so will be generically referred to herein as municipal solid waste or "MSW"), contain a tremendous amount of recyclable materials. Such materials include aluminum, iron, and diverse pulp and paper products. Environmentalists and public officials view the recycling of these materials as the most desirable method of waste disposal. According to some studies, however, curbside recycling has resulted in collection of only less than 10% of the recyclable materials. In addition to the lack of effectiveness, many people dislike the inconvenience of separating garbage, removing labels and lids, washing cans, bundling newspapers and other aspects of curbside recycling. In addition to the vast expense incurred in collecting recyclable curbside, money also must be spent on educating the public to use curbside recycling for it to be effective.

Thus there is a need to process MSW to recapture recyclable materials without the need for curbside recycling, without the need to spend funds to educate the public on its use, without the creation of harmful pollutants, and in an conically viable and repeatable industrial process.

SUMMARY OF THE INVENTION

The apparatus generally is comprised of a cylindrical vessel, containing at least one steam line for introducing steam into the interior of the vessel, and at least one valve for selectively releasing steam and/or pressure from the vessel during the process. The vessel further includes doors or hatches, or similar means to access the interior of the vessel for loading and unloading MSW. (The MSW may actually be transported to the vessel by a conveyor or other traditional means.) The apparatus includes a means for rotating the vessel, such as the use of trunnion rings and rollers, or chain-driven gear and sprocket system or "spud" ring. Any stable method of rotating the vessel at a controlled speed would be suitable. The interior of the vessel includes a structure for agitating the MSW as the vessel is rotated, such as a conical flighting or similar ridged or paddle-like structure. The apparatus further includes a boiler or other steam source for producing steam with which to heat and pressurize the vessel, and conventional steam lines, valves, and gauges for transporting, controlling, and measuring the flow of steam, temperature, and pressure. Optionally, the apparatus may include a water vamping apparatus, operatively connected to the release valve on the vessel, for evaporating and condensing the process discharge.

The process is summarized as follows. The vessel is preheated prior to loading to a predetermined preheating temperature. During loading, steam is fed into the vessel to maintain temperature, and the door at the far end of the vessel is shut during the loading process. After the vessel is loaded with MSW, the door through which the MSW was loaded is shut, steam is introduced continually into the vessel, and the vessel becomes pressurized. Fresh steam is continuously fed into the chamber from the loading end, and after a predetermined processing pressure is reached, steam is allowed to escape the chamber from the far end into the discharge steam line. The temperature and pressure of the vessel are monitored, and the flow of steam is regulated to keep the process within predetermined processing ranges (around 50 psi, 300° F.). The vessel is rotated at a predetermined speed (depending on the size of the vessel), and after a predetermined amount of time (20 to 45 minutes), the pressure is released and the processed MSW is removed.

DESCRIPTION OF THE DRAWINGS

These and other features, aspects, structures, advantages, and functions are shown or inherent in, and will become better understood with regard to, the following description and accompanied drawings where:

FIG. 1 is a perspective view of a preferred embodiment the pressure vessel of the present invention.

FIG. 2 is a sectional view of the embodiment of FIG. 1.

DETAILED DESCRIPTION OF THE PREFERRED EMBODIMENT

Figure 3:
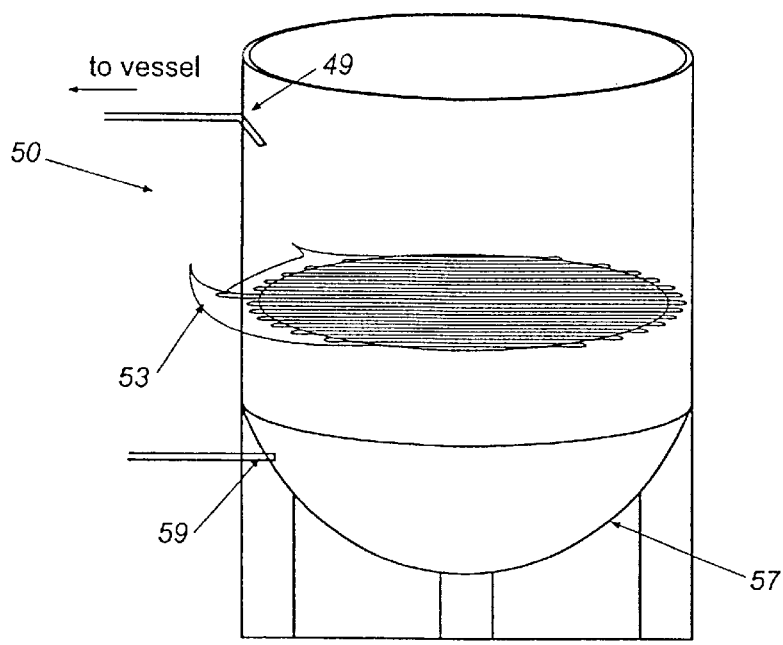
FIG. 3 is a perspective view of a preferred embodiment of a water-vamping apparatus that may be used in combination with the device shown in FIG. 1.

A preferred embodiment of the vessel 10 is depicted in FIG. 1. The vessel has a first end 17 and a second end 19. Each end has an opening which is covered by a closure member or door (the first door at the first end of the vessel and the second door at the second end of the vessel). The doors contain seals and appropriate hardware such that when they are closed the vessel may be pressurized.

The vessel has a continuous helical flighting 80 on the interior wall of the cylindrically shaped portion 15 of the vessel. This portion 15 of the vessel may be referred to as the processing chamber, and it has a first end 17 and a second end 19 which correspond to the first and second ends of the vessel. The flighting provides a means of linear conveyance as the vessel is rotated. The MSW is lifted and moved longitudinally by the flighting as the vessel rotates, until the force of gravity overcomes the frictional force and angular momentum of the MSW, in accordance with basic physical principals, causing the MSW to fall from the flighting back onto the bottom of the vessel. Optimally, the angle of the flighting and the rate of rotation of the vessel are such that the MSW lifted by a particular section of the flighting will fall into the space between and onto the next two successive sections of the flighting.

The path of the flighting may be expressed in terms of the flighting interval. The flighting interval i is defined as the distance between successive points along the flighting characterized by their intersection with a fictitious reference line that runs along the interior surface of the vessel, parallel to its longitudinal axis. (The flighting interval is somewhat analogous to the wavelength of a simple wave.) The height h of the flighting is defined as the distance from the point of contact of the flighting with the interior wall of vessel to the top of the flighting. The interval and height of the flighting are determined empirically based upon such factors as the desired degree of processing of the MSW, the desired rate of rotation of the vessel, the desired operating capacity of the vessel, the rate of circulation of MSW longitudinally during processing, and the overall size of the vessel. A decrease in the flighting interval as the flighting approaches the second end of the processing chamber affects the capacity of the vessel and the circulation of MSW within the vessel.

A plurality of steam lines 40 extend along the interior of the vessel for distributing heat and moisture throughout processing chamber. The steam lines are attached to a header 45 (see FIG. 1), made of six-inch metal pipe, which is connected via a standard flex line 41 to a rotary sealed coupling means 47 mounted first closure member. Such rotary sealed coupling means are well known in the art. The header may be round or any other desired shape (hexagonal, triangular, square, etc.). An input steam line 43 emanates from a conventional steam source such as a boiler and is attached to the rotary coupling means for introducing steam into the interior of the vessel, via the flex line, header, and steam lines, before and during the rotating process. The header becomes heated during the process, such that any steam that has condensed into water will immediately evaporate back to steam prior to introduction into the vessel. Input steam line 43 may be run at floor level and, as it approaches the vessel, make a 90° turn (perpendicular to the floor) to reach the header. At this elbow, a conventional water vamping or bleeding valve (not illustrated) is functionally attached to input steam line 43 to reduce or eliminate any liquid water that may form in the line.

A discharge steam line 49 is attached to a coupling means 47 in the second closure member for venting steam during and after the rotating process and is connected to a water vamping apparatus (described below). Discharge steam line 49 also is connected to a conventional steam source. Both input steam line 43 and output steam line 49 are operatively connected to conventional valves, gauges, and sensors for measuring and controlling temperature, pressure, and flow rate of steam in a manner that is well known in the art.

The exterior of the vessel has "trunnions" and "vacuum rings", which are placed to provide structural support. The trunnions also provide a track and contact point for rollers to enable rotation of the device. Other means of rotation, such as a chain driven gear and sprocket system or "spud" ring also would be suitable. The proper placement of the trunnions and vacuum rings longitudinally contributes to the stability and safety of the loaded vessel during operation. The exterior of the vessel need not include an insulating layer of material.

In a preferred embodiment, the processing chamber of the vessel is 60 feet long, having a diameter of 12 feet, and is made of stainless steel. The flighting interval is uniform through the majority of the processing chamber, and the interval becomes successively smaller as the flighting approaches the second end 19 of the processing chamber. In this preferred embodiment, the flighting interval is about 12 feet for a distance of approximately 45 feet from the first end of the processing chamber. This portion of the flighting has a height h of 20 inches. The flighting interval then decreases to approximately 9 feet and then to approximately 3 feet through the remainder of the processing chamber towards the second end of the vessel and into the conical portion at the second end. As the flighting interval decreases, the height h of the flighting increases from 20 inches to 26 inches towards the second end 30 of the vessel. The decreased flighting interval and increased flighting height at the second end of the vessel causes the MSW to circulate continuously from the first to the second end of the vessel as it is rotated. Ports in the steam lines 40 are of 5/16 inch diameter at the first end of the processing chamber and are decreased in size to 3/16 inch and then to 1/4 inch diameter at the second end of the processing chamber, which effects a concentration of steam toward the first end of the processing chamber. The ports 41 are 5" inches apart. If desired, the steam lines 40 may contain ports along the entire length of the vessel. These dimensions are of a preferred embodiment only, and the invention described herein is not limited to these specific dimensions.

A significant problem in the prior art relates to dealing with the large amounts of water produced by their processes. In many cases, the cost of treating the discharge water, which contains many contaminants found in MSW, made the process economically unfeasible. It is an object of the present invention to provide a solution to this water problem by routing the discharge from the process into a water vamping apparatus, described below.

Figure 4:
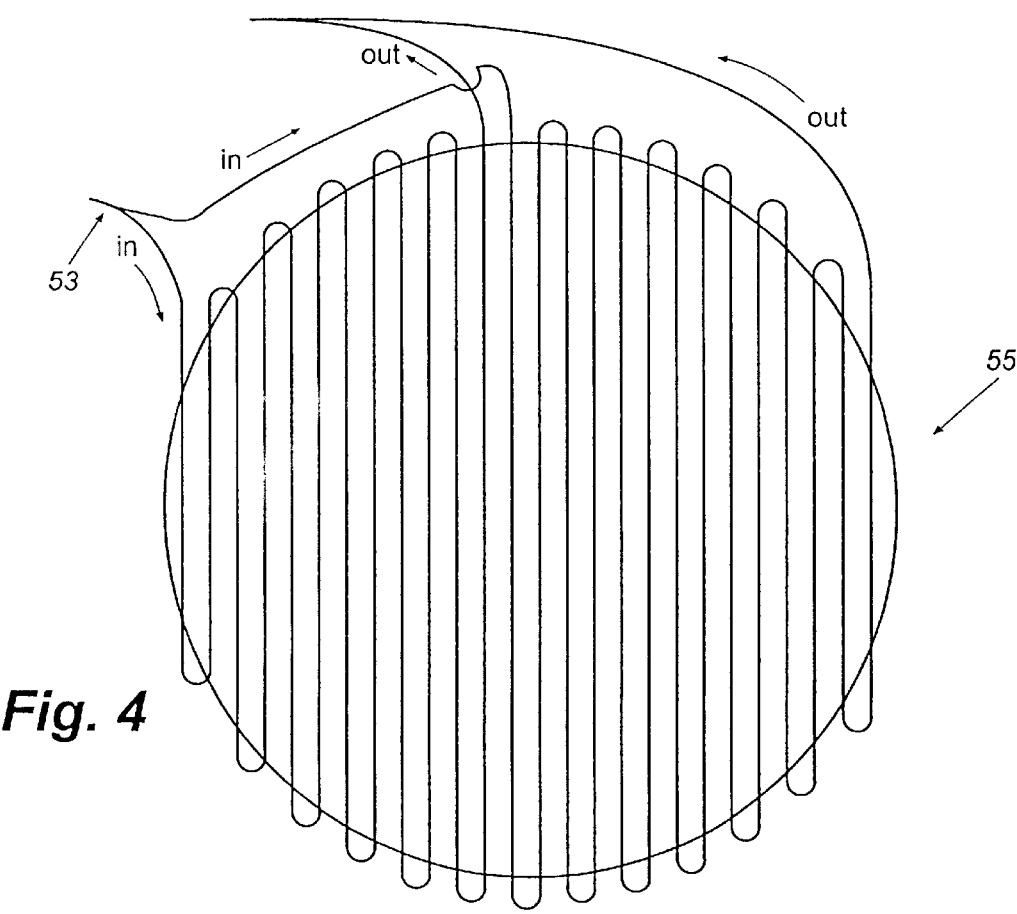
FIG. 4 is an overhead view of the heating coil of the apparatus shown in FIG. 3.

As shown in FIG. 3, a preferred embodiment of a water vamping apparatus is comprised of a large generally cylindrically shaped upright chamber 50, the upper end of which is open, and the lower end of which is closed and watertight. As shown in FIG. 4, a heat-conducting tube 53, containing steam, enters the side of the lower portion of the chamber, and the tube is shaped into a traditional coil 55 in a horizontal plane. The tube exits the chamber to return to the heat source. A second steam line, which is the discharge line 49 from the pressure vessel, enters the upper portion of the chamber in order to discharge its contents into the chamber.

The discharge from discharge line 49 contains water and steam mixed with various contaminants from the MSW treatment process, described below. The discharge falls across the heated coil 55 which evaporates a substantial portion of the water from the discharge into the atmosphere. The unevaporated discharge collects in the bottom of the chamber, reservoir 57, which may have a concave shape. A third steam line 59 enters the reservoir and is positioned with its outlet directed tangentially with respect to the arc of the inner surface of the chamber.

From time to time as the discharge that passed through heated coil 55 collects in the reservoir 57, pressurized steam is released from third steam line 59, the orientation of which causes the steam to exert a motivational force on and creates a rapid circular flow in the discharge. The rapid circular flow causes the discharge to travel up the sides of the chamber and come in contact with heated coil 55, which evaporates additional water. This process may be repeated as desired until a condensed slurry remains in the reservoir. This slurry is removed from the reservoir by a valve or other conventional means and may be chemically treated. Other means of agitating the discharge and bringing it into contact with the coil, such as a pump to lift the mixture above the coil and force it through a nozzle to disperse the discharge across the coil, may be apparent to those skilled in the art. Likewise, other means of evaporating and condensing the discharge will be apparent to those skilled in the art.

In a preferred embodiment of the process, the ambient temperature of the building should be 75–90° F. The vessel is preheated such that its exterior remains at a temperature of not less than 220° F. (the preheating temperature). During loading, steam at approximately 300° F. is introduced into the chamber from the discharge steam line (at the second end of the vessel) to maintain its heated state. An advantage of the continual introduction of steam into the vessel during loading is that the steam causes the MSW to shrink and collapse during loading, thus increasing the amount of MSW that may be loaded into the vessel without a sticking effect. The vessel is rotated in a first direction, such that material is transported to second end of the vessel during the loading process. As described above, the flighting interval is decreased as the second end, causing accumulation of the MSW there. This action causes the MSW to "back up" and begin to fill successively the spaces between the wider-spaced flightings, until the MSW backs up to the opened closure member at the first end of the vessel. If the operator attempts to load additional MSW at this point, it will fall out of the opening at the first end. Accordingly, an operator cannot overload the vessel. When the vessel is fully loaded, the first closure member is closed.

Previous processes employing rotating pressure vessels to recycle or break down MSW, as disclosed in the prior art, did not feed steam into the vessel during loading and therefore the capacity of the vessel was determined solely by the volume of the MSW loaded into it. However, MSW as received from a landfill or from households or businesses contains objects of varying volumes and densities, and the previous processes did not take this varying density into account. As a result, the amount of mass of MSW loaded into the prior art vessels was not consistent from batch to batch, and thus no single set of operating parameters would give consistent results from batch to batch. Under the loading methods of the prior art, either the process parameters (temperature, pressure, or time) had to be varied with each batch of MSW, or the consistency of the processed product (i.e., particle size, moisture content, degree of break down and processing generally) varied with batch to batch. Under such circumstances, an economically and technically viable industrial process was unobtainable. Another advantage of the continual supply of steam during loading, while simultaneously rotating the vessel, as disclosed in the present invention, is that the MSW breaks down during loading to material of roughly uniform density, so that the same mass of MSW is processed in each batch. By controlling the mass loaded into the vessel in this way, one can achieve uniform results and obtain an economically viable process in accordance with the remainder of the process disclosed herein.

After the vessel is loaded and first closure member put in the closed position, the introduction of steam from the discharge steam line is stopped, and steam is introduced into the vessel from the input steam line. The vessel is rotated in a direction opposite from direction of rotation during loading. Steam is continually added and the rate of rotation is gradually increased until the vessel is pressurized to 50 psig and achieves a final rate of rotation that is a function of the size of the vessel. In the preferred embodiment described above, the final rate of rotation is 6.25 RPM.

When the pressure in the vessel reaches 50 psig (the processing pressure), a valve controlling the discharge steam line is slowly opened, allowing steam to escape the vessel. Steam (at approximately 300° F. and 50 psig) is continually introduced into the vessel from the steam input line throughout the process.

The composition of each batch of MSW, as it is received from a landfill, will necessarily vary. As the MSW is processed, it releases varying amounts of heat or energy into the chamber, resulting in a continuously varying thermal content and pressure within the vessel. The prior art did not address this variation. This variation may be measured by measuring the temperature of the steam discharged from the process through the discharge steam line ("output temperature"). If the variation in content is not somehow taken into account, the temperature and pressure in the vessel will vary widely from batch to batch of MSW, again affecting the consistency of the resulting cellulose product. In order to accommodate this variation, it is necessary to monitor the output temperature of the process and adjust the flow of steam through the input steam line during the process.

It has been determined that for optimal results the output temperature should be kept in the range of approximately 290–320° F. (the processing temperature range). This temperature is controlled by varying the flow of steam into the vessel from the input steam line. For example, as the output temperature approaches 320° F., the flow rate of steam into the vessel is decreased, and conversely as the output temperature approaches 290° F., the input flow rate is increased. Within these parameters the internal pressure of the vessel ranges from approximately 50–60 psig, though it may at times be as low as 45 psig or as high as 65 psig (the processing pressure range).

Discharge from the process is released through the discharge steam line into the water vamping chamber as described more fully above.

The MSW is rotated and subjected to the above temperature and pressures for approximately 30 minutes. The second closure member is then opened, and the vessel is rotated in a direction such that the processed MSW is transported by the flighting towards the second end of the vessel, which facilitates unloading of the processed MSW.

The processed MSW is then transported to conventional means for separating and classifying its constituent parts.

It is apparent that while specific embodiments of the invention is disclosed, various modifications of the apparatus or parameters of the process may be made which will be within the spirit and scope of the invention. Therefore the spirit and scope of the present invention should be determined by reference to the claims below.

What is claimed is:

1. A method of processing solid waste products containing pulp and paper products in a vessel comprising:
   preheating the vessel to a predetermined preheating temperature by introducing steam into its interior;
   rotating the vessel;
   loading the vessel with solid waste products;
   sealing the vessel and continuing to introduce steam thereinto until a predetermined processing pressure is reached;
   thereafter controllably discharging steam from the vessel;
   monitoring the temperature of the discharged steam and regulating the flow of steam introduced into the vessel such that the temperature of the discharged steam and the internal pressure of the vessel each stay within a predetermined processing range;

after a predetermined period of time, depressurizing the vessel and unloading the processed waste therefrom.

2. The method of claim 1, wherein the predetermined preheating temperature is about 220° F.

3. The method of claim 1, wherein the predetermined processing temperature is about 300° F.

4. The method of claim 3, wherein the temperature range of the discharged steam is in the range of 290° F. to 320° F.

5. The method of claim 4, wherein the internal pressure of the vessel during the monitoring step is in the range of 45 psi to 65 psi.

6. The method of claim 5, wherein the internal pressure is maintained at 50 psig.

7. The method of claim 5, wherein the predetermined period of time is about 30 minutes.

8. The method of claim 1, said vessel having a diameter of twelve feet; wherein in the vessel is rotated at 6.25 rotations per minute in the second direction.

9. The method of claim 1, further comprising:

routing the discharged steam away from the vessel;

allowing at least a portion of the discharged steam to condense into a liquid state, thus forming a mixture of steam and liquid; and passing the mixture over an evaporating means, such that a substantial portion thereof is converted to a gaseous state and evaporated.

10. The method of claim 9, further comprising:

collecting the unevaporated portion of the mixture in a reservoir, said unevaporated portion being a slurry of water and residue of said waste products;

passing the slurry over the evaporating means, such that water is evaporated from said slurry.

11. The method of claim 10, further comprising chemically treating and disposing of said slurry.

12. A method of processing solid waste products containing pulp and paper products in a cylindrical vessel, said vessel having a proximate end and a distal end and a flighting for conveying said products longitudinally within said vessel, said method comprising:

preheating the vessel to a predetermined preheating temperature by introducing steam into its interior;

loading the vessel at its proximate end with solid waste products while rotating the vessel in a first direction such that said waste products are conveyed by said flighting to the distal end of said vessel;

sealing the vessel and continuing to introduce steam thereinto until a predetermined processing pressure is reached;

rotating the vessel in a second direction opposite the first direction;

thereafter controllably discharging steam from the vessel;

monitoring the temperature of the discharged steam and regulating the flow of steam introduced into the vessel such that the temperature of the discharged steam and the internal pressure of the vessel each stay within a predetermined processing range;

after a predetermined period of time, depressurizing the vessel and unloading the processed waste therefrom.

13. The method of claim 12, wherein in the preheating step, the steam is introduced into the vessel from its distal end; and in the loading step, continuing to load the waste products into the vessel until the waste products are no longer conveyed away from the proximate end of the vessel.

14. An apparatus for processing solid waste products containing pulp and paper products, said apparatus comprising:

a cylindrical vessel having a proximate end, and a distal end, each said end terminating in a hatch that may be opened to allow access to the interior of said vessel and sealably closed to allow pressurization of said vessel;

means for conveying said waste products longitudinally within said vessel;

means for controllably introducing steam into said vessel and for monitoring the temperature of said introduced steam;

a header, said header comprising heat conductive piping and coupled to said steam-introducing means;

means for monitoring the interior pressure of said vessel;

means for controllably discharging steam from said vessel and monitoring the temperature of said discharged steam;

means for controllably rotating said vessel.

15. The apparatus of claim 14, wherein the conveying means is a helical flighting attached to the interior wall of said vessel.

16. The apparatus of claim 15, said flighting having a flighting interval wherein said flighting interval decreases as said flighting approaches the distal end of said vessel.

17. The apparatus of claim 15, said flighting having a flighting height, wherein said flighting height increases as said flighting approaches the distal end of said vessel.

18. The apparatus of claim 17, said flighting having a flighting interval, wherein said flighting interval decreases as said flighting approaches the distal end of said vessel.

19. The apparatus of claim 14, wherein said steam introducing means comprise a plurality of steam lines extending longitudinally along the interior of said vessel, said steam lines having a plurality of ports for releasing steam into said vessel, said ports decreasing in size from the proximate end to the distal end of said vessel.

20. The apparatus of claim 14, wherein said steam discharging means comprises an output steam line, said apparatus further comprising:

a water vampings apparatus, said vamping apparatus comprising an upright tank having side walls, an open top and a closed bottom, and evaporating means positioned above said closed bottom, said steam line opening into said tank above said evaporating means, whereby discharge of said steam line falls across said evaporating means and at least a portion thereof is evaporated, the unevaporated portion falling into and collecting in the bottom of said tank.

21. The apparatus of claim 20, wherein said evaporating means is a heated coil.

22. The apparatus of claim 21, further comprising means for passing said unevaporated portion over said coil.

* * * * *